United States Patent [19]

Fehr

[11] 4,334,543

[45] Jun. 15, 1982

[54] METHOD AND APPARATUS FOR FLOW VELOCITY DETERMINATION

[75] Inventor: Rainer Fehr, Reinach, Switzerland

[73] Assignee: Hoffmann-La Roche Inc., Nutley, N.J.

[21] Appl. No.: 97,978

[22] Filed: Nov. 28, 1979

[30] Foreign Application Priority Data

Dec. 4, 1978 [CH] Switzerland ............... 12361/78

[51] Int. Cl.³ ............................................ A61B 10/00
[52] U.S. Cl. .................................. 128/663; 73/861.25
[58] Field of Search ............. 128/663; 73/861.25; 343/5 NQ, 8; 364/509, 510, 730; 367/90

[56] References Cited

U.S. PATENT DOCUMENTS

3,914,999 10/1975 Grandchamp ............... 128/663 X

OTHER PUBLICATIONS

Brondestini, M., "Topoflow-A Digital Full-Range Doppler Velocity Meter", IEEE Trans. on Sonics and Ultra-sonics, vol. SU-25, No. 5, Sep. 1978, pp. 287-293.
Hartley, C. J. et al., "A Single-Crystal UTS Catheter-Tip Velocity Probe", Jrnl. Assoc. Advancement Med. Instramentation, vol. 8, No. 4, Jul.-Aug. 1974, pp. 241-243.
Doriot, P. A. et al., "Quant. Anal. of Flow Cond. in Simu. Vessels & Large Human Arteries and Veins by Means of Ultrasound", Conf. Proc. Zd. Eur. Cong. on UTS in Med., Munich, 12-16 May 1975, pp. 160-168.
Grandchamp, P. A., "A Novel Pulsed Dir. Doppler Velocimeter: Phase Det. Profilometer," Conf. Proc. Zd. Eur. Cong. on UTS in Med., Munich, 12-16 May 1975, pp. 137-143.
Fehr, R. et al., "Pulsed UTS Doppler Velocimeter for Measuring Velocity Profiles by Analog Sig. Proc. Methods", Biomed. Technik, vol. 21, (supp.), Jun. 1976, pp. 289-290.
Brondestini, M., "A Digital 128-Channel Transcutaneous Blood-Flowmeter", Biomed. Technik, vol. 21, (supp.), pp. 291-292, Jun. 1976.
Brondestini, M., "UTS Blood Flowmeter Yielding Instantaneous Velocity Profile by Real Time Phase Det.", Elec. Letters, vol. 11, No. 8, pp. 183-184, 17 Apr. 1975.
Brondestini, M., "Appl. of Phase Det. Principle in a Transcut. Vel. Profile Meter," Conf. Proc. Zd. Eur. Cong. on UTS in Med., Munich, 12-16 May 1975, pp. 144-152.

*Primary Examiner*—Robert W. Michell
*Assistant Examiner*—Francis J. Jaworski
*Attorney, Agent, or Firm*—Jon S. Saxe; Bernard S. Leon; George M. Gould

[57] ABSTRACT

A method of determining flow velocities by measuring the phase difference between Doppler signals derived from wave pulses and reflected by substantially the same reflector at two different times, the interval between the times being predetermined, a pair of electric signals being derived according to the method from each Doppler signal by modulation in quadrature, the signals jointly bearing information relating to the phase of the Doppler signal, and a device for performing the method. In order to make full use of the possible measuring range, even at a relatively poor signal/noise ratio, at least a first and a second pair of signals are combined to form a third pair of electric signals which together bear an item of information depending on the phase difference between the Doppler signals. Mean-value signals are formed, each corresponding to the mean value of one of the third pair of signals, and an output signal which corresponds to the mean value of the phase difference between the Doppler signals is derived from the mean-value signals. It is particularly advantageous to use the method in an ultrasound diagnostic device for determining the velocity profile of a flow, more particularly of blood in a blood vessel.

9 Claims, 33 Drawing Figures

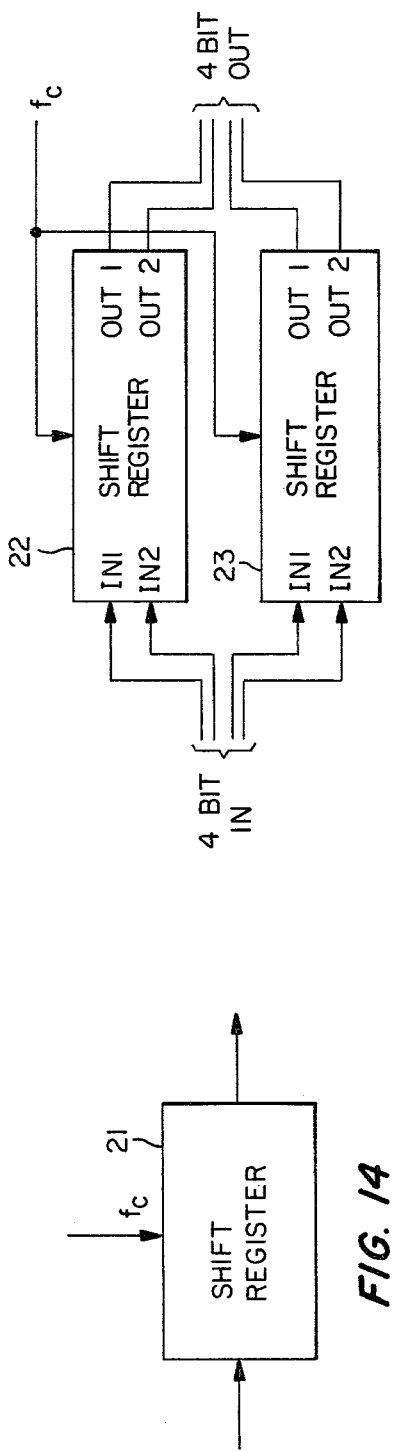
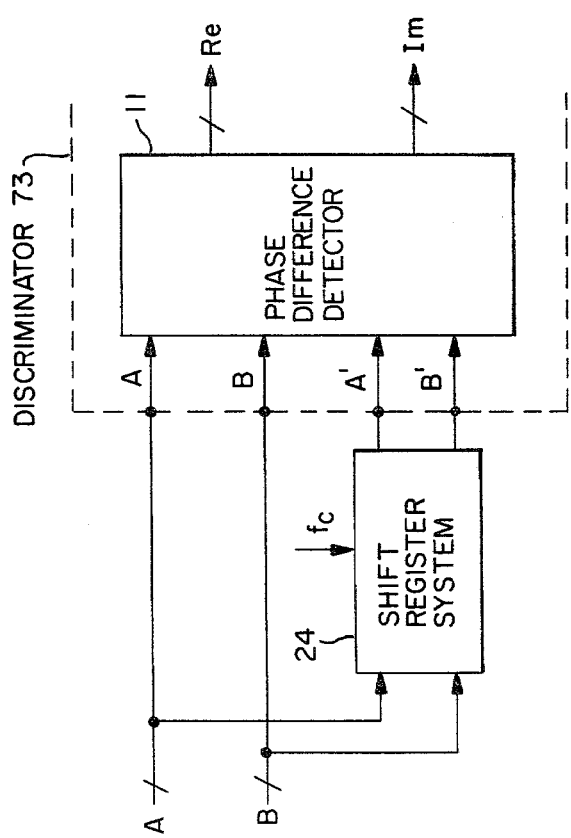

FIG. 25

METHOD AND APPARATUS FOR FLOW VELOCITY DETERMINATION

BACKGROUND OF THE INVENTION

The invention relates to a method of determining flow velocities by measuring the phase difference between Doppler signals derived from wave pulses and reflected by substantially the same reflector at two different times, the interval between the times being predetermined, a pair of electric signals being derived according to the method from each Doppler signal by modulation in quadrature, the signals jointly bearing information relating to the phase of the Doppler signal. The invention also relates to a device for performing the method.

In a known method of the aforementioned kind (U.S. Pat. No. 3,914,999), the instantaneous value of the projection of the point velocity in a given direction X is determined from the formula $V_x = k\Delta\phi/\Delta t$ where k is the proportionality constant, $\Delta\phi$ is the phase difference between the Doppler signals and $\Delta t$ is an integral multiple of the pulse repetition frequency.

In order to improve the signal/noise ratio, the measured results are averaged over a certain time, in which case we have:

$$V_x \propto \frac{1}{n} \cdot \sum_{k=1}^{n} \frac{\Delta\phi}{\Delta\tau} k \text{ where } \Delta\phi_k = \phi_{k+1} - \phi_k$$

where $\phi_k$ is the phase of the Doppler signal after the $k^{th}$ transmitted pulse, if $\Delta t = 1/\text{PRF}$ (PRF=pulse repetition frequency).

When the velocity profile of a blood flow is transcutaneously measured by the aforementioned method, the problem arises of determining the average phase difference $\overline{\Delta\phi}$ between the Doppler signals with maximum accuracy and in a given time, at a poor signal/noise ratio. (The reason why the signal/noise ratio is poor is easy to understand, since the echoes from blood corpuscles are naturally much weaker than from stationary surrounding structures). To solve this problem it has already been suggested (M. Brandestini, "Topoflow-A Digital Full Range Doppler Velocity Meter", IEEE Transactions on Sonics and Ultrasonics, September 1978, Vl. Su-25, No. 5, pp. 287-293) to use a discriminator comprising a "zero crossing detector" upstream of a sweep integrator. This latter discriminator, which in fact does not determine the average phase difference $\overline{\Delta\phi}$, but an average of the Doppler frequency shift, has the following advantages:

1. The desired linear relation between the phase difference and the output value from the discriminator does not extend over the theoretically possible range of $2\pi$.
2. A decreasing signal/noise ratio results in systematic distortion of the characteristic, resulting in uncontrollable measuring errors in practice.
3. Only scalar values of the phase difference are determined, so that the sign of $\Delta\phi = \pi$ is not defined.

SUMMARY OF THE INVENTION

The aim of the invention is to eliminate these disadvantages.

To this end, according to the invention, at least a first and a second pair of signals are combined to produce a third pair of electric signals which together bear an item of information depending on the phase difference between the Doppler signals, mean-value signals are formed, each corresponding to the mean value of one signal from the third pair, and an output signal which corresponds to the mean value of the phase difference between the Doppler signals is derived from the mean-value signals.

The invention also relates to a device for performing the method according to the invention, comprising a circuit for combining the first and second pair of signals to produce the third pair, means for forming the mean-value signals, each corresponding to the mean value of one of the third pair of signals, and a computer unit for processing the mean-value signals to obtain an output signal corresponding to the mean phase difference between the Doppler signals.

The invention also relates to the use of the method according to the invention in an ultrasonic diagnostic device for determining a velocity profile of a flow, more particularly of blood in a blood vessel.

The main advantages of the method according to the invention are that the results are substantially free from systematic errors and full use is made of the theoretical maximum measuring range.

BRIEF DESCRIPTION OF THE DRAWINGS

Some embodiments of the invention will now be described with reference to the accompanying drawings, in which:

FIG. 14 shows a generalized diagram of a shift register digital delay line;

FIG. 15 shows the details of the shift register digital delay line in FIG. 14;

FIG. 16 shows circuits connected immediately upstream and downstream of the inputs of discriminator 73;

FIG. 17 is a truth table for combining binary-coded input signals in the phase difference detector 11;

FIG. 25 shows the truth table for combining ternary-coded input signals in the phase difference detector 11;

DESCRIPTION OF THE PREFERRED EMBODIMENTS

Figure 1:
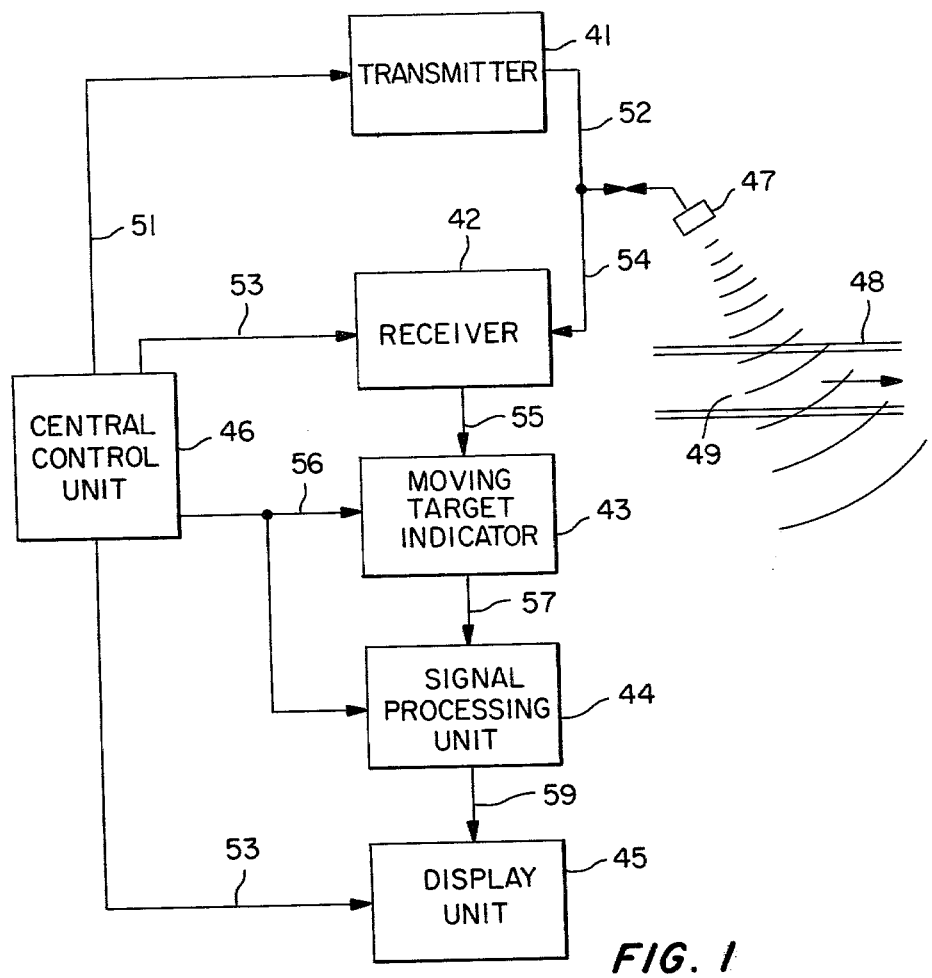
FIG. 1 is a block circuit diagram of an ultrasound Doppler device for determining the velocity profile of a flow.

FIG. 1 is a block circuit diagram of an ultrasonic Doppler device for determining the velocity profile of a fluid (e.g. a liquid such as blood or a gas such as air). The principle of this device is disclosed in U.S. Pat. No. 3,941,999. According to this known principle, a fluid 49 flowing e.g. through a tube 48 is irradiated by two successive ultrasound pulses emitted by a transducer 47. The corresponding Doppler frequency-shifted echoes from reflectors in the fluid along the ultrasound beam are received by transducer 47 and a signal 59 is obtained by suitable processing from the differences between echoes having equal transit times and resulting from the first and second transmitted ultrasound pulses, the variation in time of signal 59 corresponding to the velocity profile of the fluid in the cross-section under observation. In the circuit in FIG. 1, the aforementioned signal processing is brought about by a receiver 42 connected in series with a moving target indicator 43 and a signal processing unit 44, which deliver the signal 59 corresponding to the velocity profile to a suitable display unit 45, e.g. a cathode-ray oscillograph. A central control unit 46 controls the units in the circuit in FIG. 1.

Figure 2:
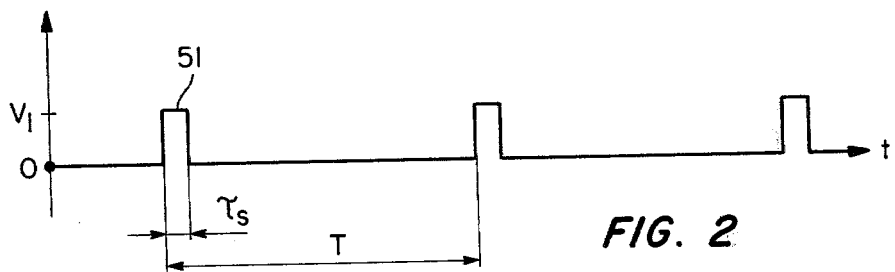
FIGS. 2,3,4,5a,5b and 6 show in outline typical signal curves at a number of points in the circuit diagram of FIG. 1.
Figure 3:
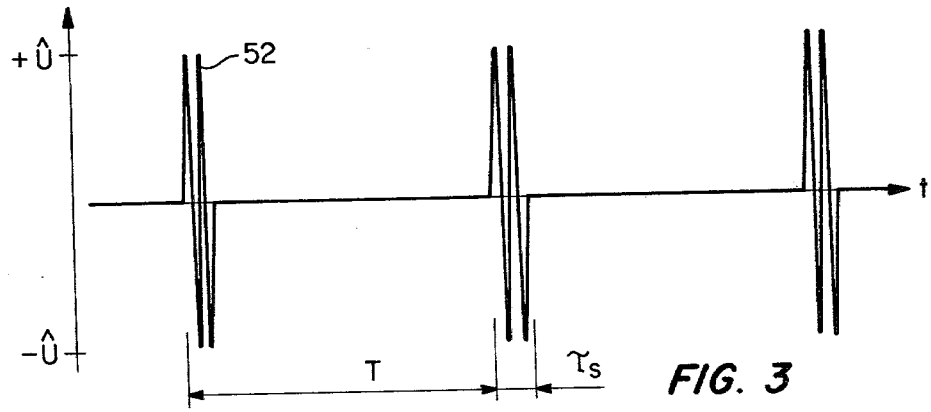

During operation, control pulses 51 from unit 46 stimulate transmitter 41 so that it transmits pulses 52 to transducer 47. The control pulses 51 (see FIG. 2) have a duration $\tau_s$ of e.g. 0.5 µs and a pulse repetition period T=100 µs. The corresponding transmitter pulse 52 (see FIG. 3) are wave pulses at a transmitter voltage $\hat{U}=20$ V and a transmitted frequency fo=4 MHZ, so that in the present example the number of transmitted oscillations per pulse is fo.$\tau_s$=2.

Figure 4:
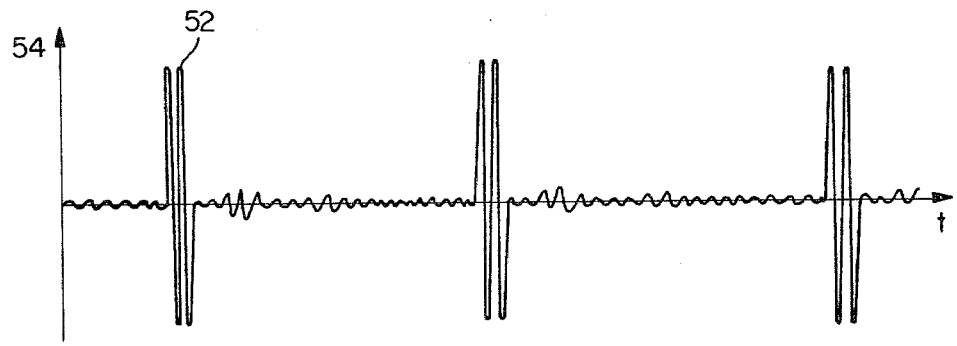

FIG. 4 shows a typical input signal 54 of receiver 42, consisting of transmitted pulses 52 and various Doppler-frequency echo signals.

Figure 5A:
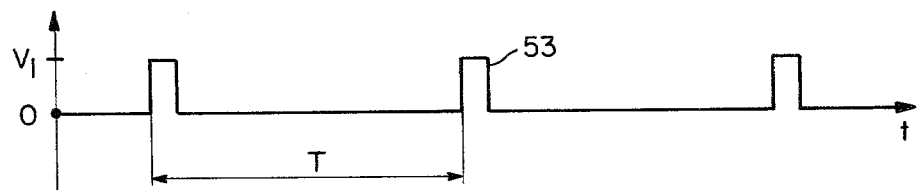
Figure 5B:
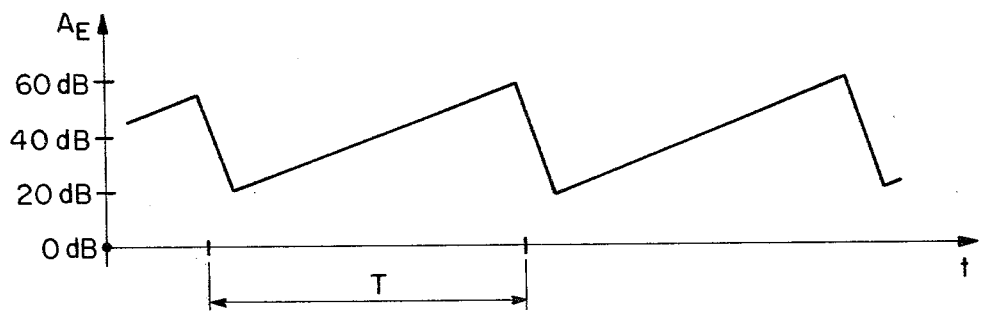
Figure 6:
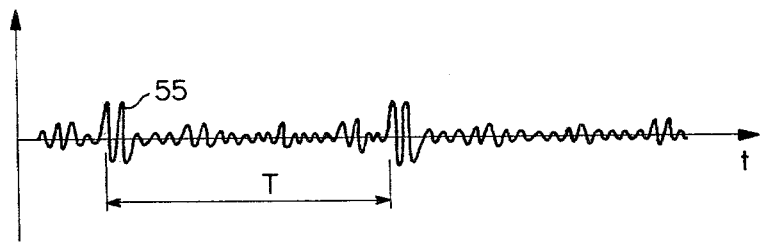

Since the amplitude of the echo signals from transducer 47 to receiver 42 depend on the distance between the transducer and the corresponding reflector and thus depend on the transit time, i.e. on the time between the transmission of a transmitted pulse and the reception of the echo from the reflector, the amplification of signal 54 in the receiver is adjusted so as to eliminate the attenuation caused by the distance between the transducer and the corresponding reflector. As FIGS. 5a and 5b show, the variation in the controlled amplification $A_E$ in receiver 42 is synchronized with the transmitted pulses by control pulses 53. The amplitude of the transmitted pulses contained in the received signal 54 is also limited in receiver 42. FIG. 6 diagrammatically shows the curve of a typical receiver output signal 55 produced by the aforementioned method (controlled amplification and limitation).

The output signal 55 consists of Doppler frequency-shifted echo signals bearing the velocity information, and echo signals produced by relatively immovable body structures, e.g. the wall of a blood vessel when the velocity profile of the blood stream is being measured. The last-mentioned echo signals (also called "stationary" echo signals or "permanent echoes") are usually strong interfering signals on which the relatively weak Doppler frequency-shifted echo signals are superposed. In order, therefore, to generate velocity profiles by the methods disclosed from U.S. Pat. No. 3,914,999 (corresponding to German Offenlegungsschrift No. 24 06 630), it is necessary to use a periodic filter 43 such as a MTI, i.e. a moving target indicator (the conventional name in radar technology) so as to separate the weak Doppler frequency-shifted echo signals from the much stronger, superposed stationary echo signals. The moving target indicator in this method is preferably the filter system described in German Offenlegungsschrift No. 27 03 879. At each place in the fluid along the ultrasound beam, the moving target indicator greatly attenuates the stationary echo components but transmits echo signals at low Doppler frequencies practically without attenuation, so that very sensitive, accurate measurements can be made of low flow velocities, i.e. the velocity profile of a flow.

Figure 7:
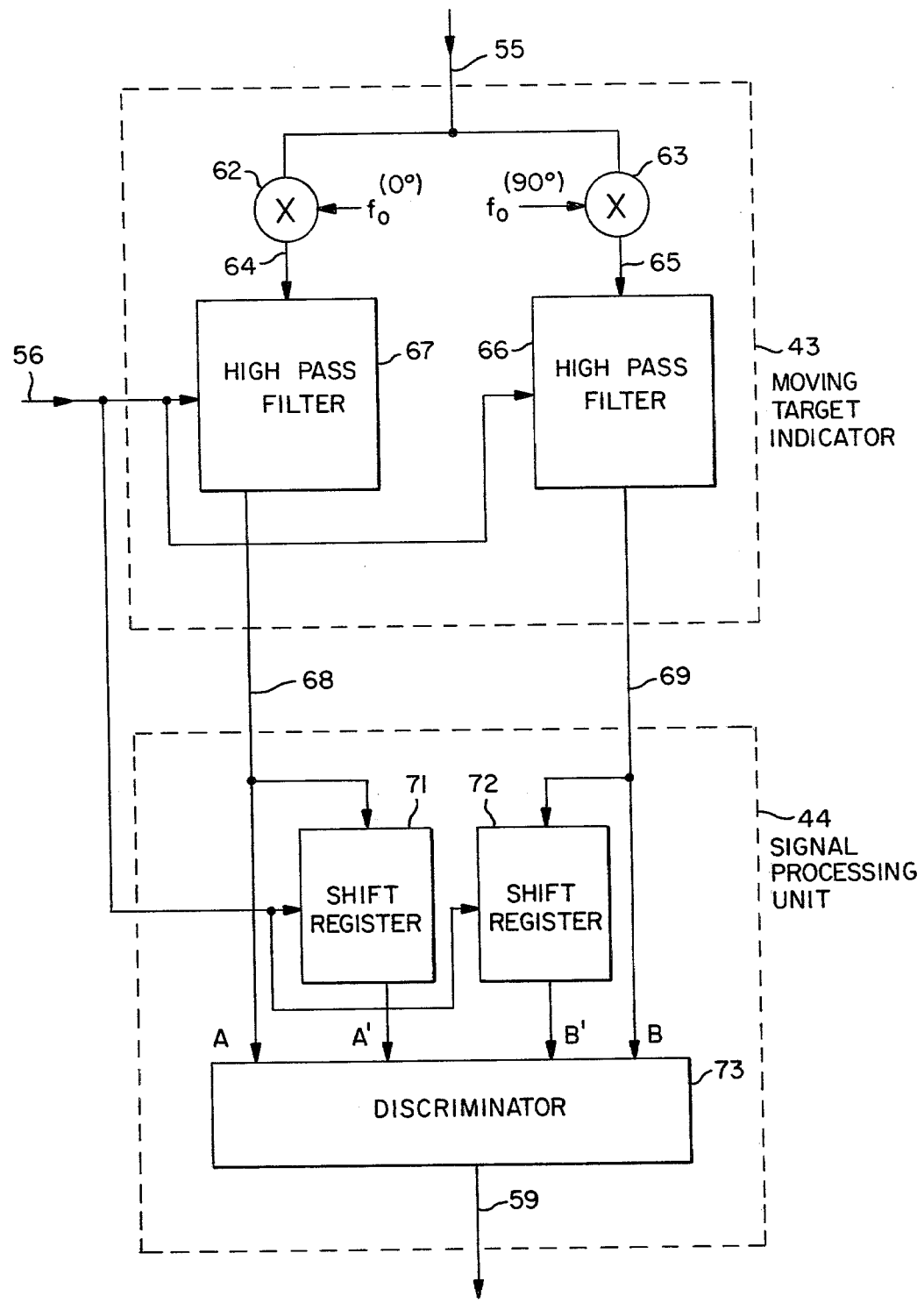
FIG. 7 is a block circuit diagram of the moving target indicator 43 and the signal processing unit 44 in the device in FIG. 1.

FIG. 7 is a more detailed view of the moving target indicator 43 and the signal processing unit 44 in the system in FIG. 4.

The moving target indicator 43 contains two synchronous demodulators 62, 63 and two periodic high-pass filters 66, 67 according to German Offenlegungsschrift No. 27 03 879. As FIG. 7 shows, the input signal 55 of MTI 43 is demodulated in quadrature by means of demodulators 62 and 63, i.e. the input signal 55 is multiplied by two reference signals fo (0°) and fo (90°) phase-shifted by 90° relative to one another, to obtain two low-frequency signals 64 and 65. Since higher frequencies are also produced during demodulation, the demodulators contain low-pass filters which transmit only the low-frequency signals 64 and 65. Quadrature demodulation is suitable for the following reasons. It is necessary for determining the velocity profile of a flow, using a Doppler device, if the direction of flow has to be determined from the demodulated signal. Quadrature demodulation is also advantageous, if as in the present case, the moving target is indicated by means of a second filter, since both the scanning frequency of the filter and the number of required storage spaces can be kept at a minimum by quadrature demodulation.

Figure 8:
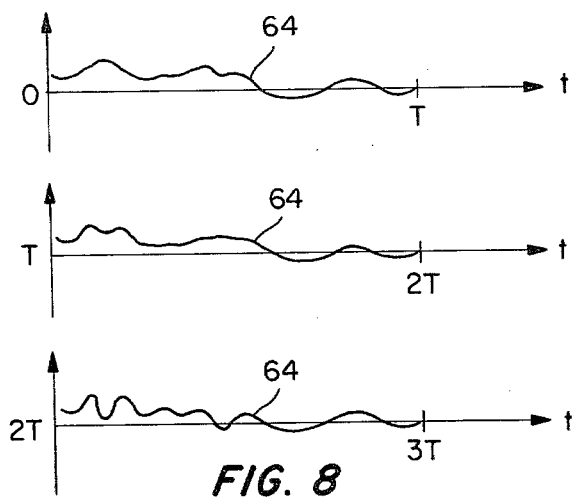
FIGS. 8, 9, 10 and 11 diagrammatically show the signal curves at a number of places in the circuit diagram of FIG. 7.
Figure 9:
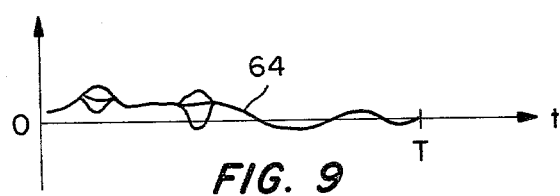

The moving target indicator 43 operates as follows:

FIG. 8 is a diagram of the demodulated signal 64 at the input of filter 67. The demodulated signal 65 at the input of filter 66 has the same appearance as signal 64 except that the Doppler oscillation is phase-shifted by +90° or −90°, depending on the direction of flow. In FIG. 8, the echo trains from a number of successive pulses are shown separately. FIG. 9 shows the same echoes when superposed. For simplicity, FIG. 9 shows only two places where Doppler oscillation occurs, whereas the rest of the echo signal curve remains stationary.

Signal processing in the periodic high-pass filters 66, 67 is described in detail in German Offenlegungsschrift No. 27 03 879. The output signals 68, 69 of filters 66, 67 will now be described with references to FIGS. 10 and 11.

Figure 10:
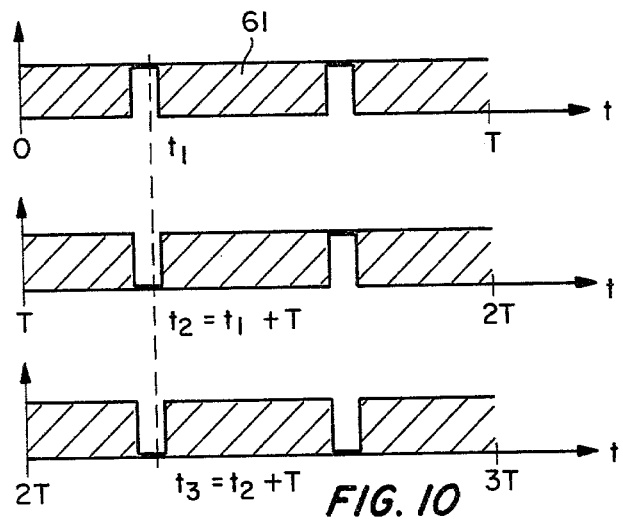

Since the output signals have practically the same wave-form and differ only in phase, FIG. 10 by way of example shows the output signal 68 of filter 67 in FIG.

7. The scanned values correspond in sign to the Doppler oscillations shown in FIG. 9. As shown in FIG. 10 in the case of the first Doppler oscillation, the values are scanned at a given place on the velocity profile, using a transmitted ultrasound pulse having the period T. Each scanned value is e.g. a one-bit signal having the same duration as a scanning pulse. By means of the moving target indicator, both Doppler ocsillations in FIG. 9 can be detected. In FIG. 10 the shaded regions 61 are indeterminate since, if no Doppler oscillations are available, the sign of the output signal 68 is not unambiguously defined, because the output signals 68, 69 are near zero and overlaid by interfering signals.

Figure 11:
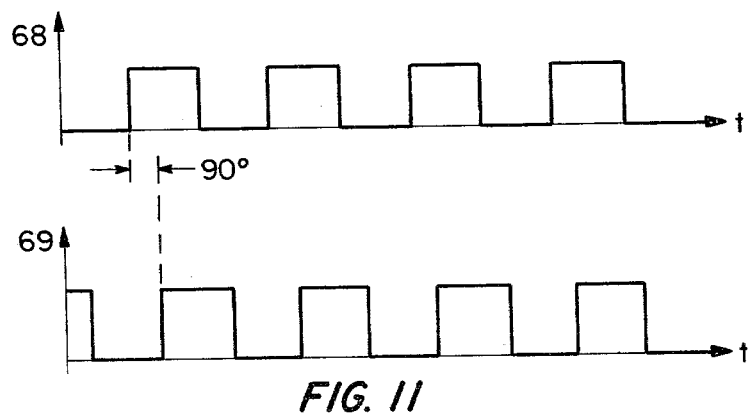

FIG. 11 diagrammatically shows the shape of the output signals 68, 69 of filters 66, 67 (in FIG. 7), assuming that a Doppler frequency is scanned at only one place on the velocity profile. This assumption simplifies the representation of the output signals 68, 69. The direction of the phase shift between the otherwise similar signals 68, 69 corresponds to the sign, i.e. the direction, of the instantaneous velocity at the place under observation. Owing to the quadrature modulation, signals 68, 69 are orthogonal vector components of the Doppler oscillation vector.

As shown in FIG 7, the output signals 68, 69 of the moving target indicator 43 are processed in unit 44, where the output signals 68, 69 are delayed by delay means, e.g. sift registers 71 and 72, by a pulse repetition period and are processed in a discriminator 73 with non-delayed output signals 68 and 69 by a method described hereinafter to obtain an analog output signal 59 corresponding to the mean value $\overline{\Delta\phi}$ of the phase difference between input signals 55, corresponding to echoes (equal transit time) of two different transmitted pulses. The wave-form of the resulting output signal 59 corresponds to the velocity profile of flow in the plane scanned with ultrasound pulses.

At the input of discriminator 73 in FIG. 7, the non-delayed signals 68, 69 are called A and B whereas the delayed signals are called A' and B'.

As shown in FIG. 1, the horizontal deflection of display device 45 is synchronized with the pulse repetition frequency by control pulses 53 (the same as for controlling the receiver 42).

Figure 12:
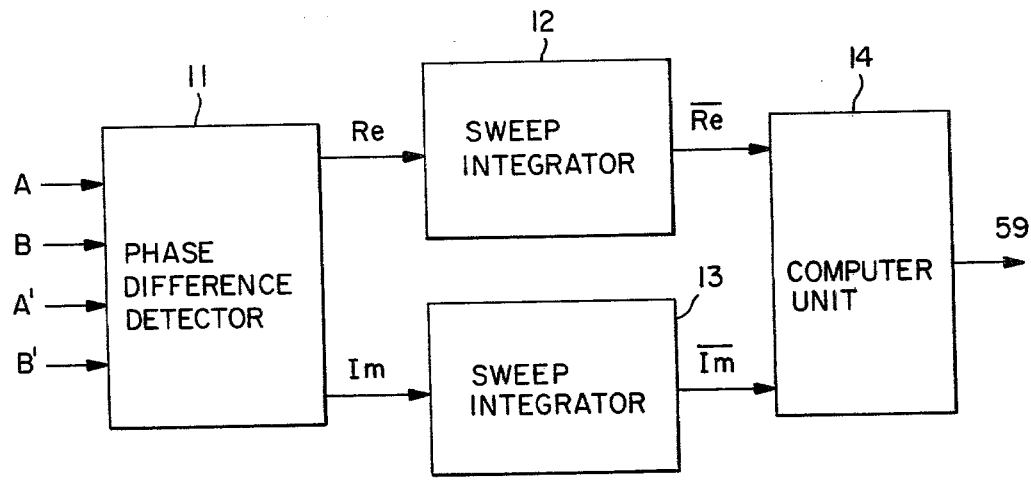
FIG. 12 shows a block diagram of discriminator 73 in FIG. 7.

FIG. 12 shows the basic structure of discriminator 73 in FIG. 7. In the discriminator, the input signals A, B and A', B' are processed in three stages.

Owing to the quadrature modulation brought about in the moving target indicator 43 (see FIG. 7), signals A, B and A', B' are orthogonal vector components of corresponding Doppler oscillation vectors, i.e. vectors which each represent a Doppler oscillation. Accordingly, A, B and A', B' each define a signal vector.

A phase difference detector 11 generates two output signals Re and Im which define a phase difference vector $\overrightarrow{\Delta\phi}$ having a modulus of unity and a phase equal to the phase difference between the signal vectors, which are defined by A, B and A', B'.

In general information expressed mathematically, the phase difference detector is used to form a complex number $$Z_1 = A + jB,$$

$$Z_2 = A' + jB'$$

from each of the input signals A, B and A', B' respectively; by forming the quotient $Z_1/Z_2$ it forms a complex number whose components Re and Im are identical with the components of the phase difference vector $\overrightarrow{\Delta\phi}$, and generates output signals corresponding to the components Re and Im respectively. A phase difference detector of this kind can be constructed with various circuits. The simplest embodiments will now be described with reference to FIGS. 17–21. General embodiments will be described later with reference to FIGS. 31 and 32.

Figure 13:
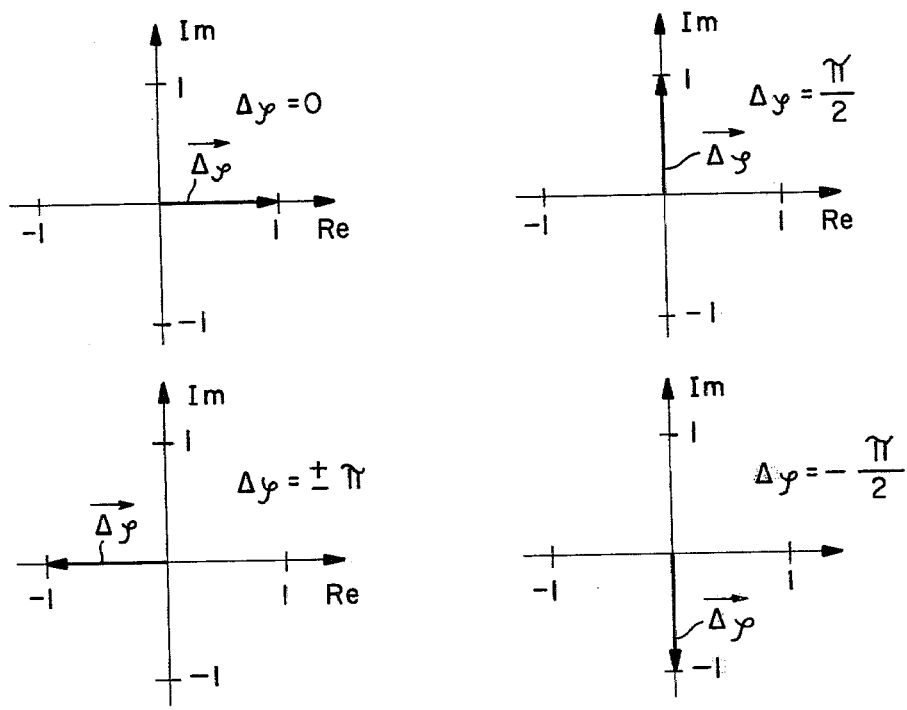
FIG. 13 shows four possible phase difference vectors.

If we work with limited, scanned signal vectors A, B and A', B', there are four possible phase difference vectors. These are shown in FIG. 13, in which each of the four vectors are defined by two components Re $(\overrightarrow{\Delta\phi})$ and Im $(\overrightarrow{\Delta\phi})$. In the known method (M. Brandestini, "Topoflow—A Digital Full Range Doppler Velocity Meter", IEEE Transactions Sonics and Ultrasonics, September 1978, Vol. SU-25, No. 5, pp. 287–293) only a scalar value of the average Doppler frequency shift is found, so that the value thereof which corresponds to $\Delta\phi = \pi$ is of litte use, owing to its unknown sign. In the present method, on the other hand, all phase difference vectors are completely defined in magnitude and sign.

In the second part of the system in FIG. 12, the output signals Re and Im of the phase difference detector are averaged by suitable means, e.g. two identical periodic low-pass filters or "sweep integrators" 12 and 13. The output signals $\overline{Re}$ and $\overline{Im}$ of these filters correspond to the average value of Re and Im. $\overline{Re}$ and $\overline{Im}$ define the average phase difference vector.

The computer unit 14 forming the third part of the system in FIG. 12 generates the discriminator output signal 59. Computer unit 14 generates a signal corresponding to the phase of the average phase difference vector for each point of the velocity profile to be measured, and the signal is used to obtain the output signal 59, whose wave-form corresponds to the velocity profile, i.e. the spatial distribution of the measured instantaneous velocities.

In accordance with the averaging time, the phase of the mean phase difference vector is more finely defined than at the output of the phase difference detector and there is thus a corresponding reduction in the region around $\pi$ where the sign is uncertain.

If the signal/noise ratio of the input signal becomes worse, it reduces the accuracy of the measurement. This is shown by a reduction in the averaged "phase difference vector" and in a statistical fluctuation in its phase. However, no systematic phase error occurs, because the phase of pure noise is completely random and does not have any preferred value at which it can converge.

The main difference between the previously-known method and the new method described here can be summarized as follows:

Since each instantaneous velocity corresponds to the Doppler frequency $f_D$ of echo values coming from a point, the method mentioned in the introduction to the present description can be used to generate a signal which corresponds to the echo signals over a certain range of the Doppler frequency.

The main problem in determining the Doppler frequency by the known method is in relating the frequency, which is an aperiodically varying quantity, to the phase difference, which is a periodically varying quantity.

In the known method, the corresponding Doppler frequency $f_D = \Delta\phi_k/\Delta t$ is derived for each phase difference $(\Delta\phi_k)$ and the average out of a number (e.g. 100) of derived Doppler-frequency values is calculated. The calculation of $f_D = \Delta\phi_k/\Delta t$ is difficult if $\Delta\phi$ is approximately equal to $\pi$. If $|\Delta\phi|$ has a wide statistical range of fluctuation as a result of noise, it may not be possible for a region corresponding to the maximum fluctuation range around $\Delta\phi = \pi$ to be unambiguously assigned to the frequency. The result will be a decrease in the permitted $\Delta\phi$, depending on the noise and thus, considerably restricting the measuring range.

In the novel method described here, the components of the phase difference vector (and thus the vector itself) are averaged before the Doppler frequency (which is proportional to the point velocity) is derived therefrom. As a result, the range of fluctuation of $\Delta\phi$ is greatly reduced and the prior art restriction in the measuring range can be almost completely avoided in practice.

Embodiments of discriminators 73

The following is a description of two embodiments of discriminator 73 which work with binary (two-value) or ternary (three-value) limitation of the input signals A, B and A', B'.

As FIGS. 1 and 7 show, an ultrasound pulse echo device is a source for signals A and B. The device transmits ultrasound pulses having the pulse repetition frequency $f_R$ (typically 10 kHz). The time between transmitted pulses is divided into N equal intervals by the timing frequency $f_c \cdot f_c$ is the scanning frequency and is chosen in accordance with the desired spatial resolution (typically $f_c = 1.28$ MHz). N is the number of storage spaces used in all digital delay lines adapted to delay the signal by a full pulse repetition period (typically $N = 128$).

The signal delays mentioned hereinafter can be brought about by shift registers or digital stores (semiconductor stores and core stores).

FIG. 14 is a block circuit diagram of a shift register 21 for 4-bit input and output signals, with a storage capacity of $4 \times N$ bits. FIG. 15 shows an example of the structure of the shift register 21, if it is constructed by means of the TMS 3114 integrated circuit manufactured by Texas Instruments and contains two shift registers 22, 23 each with 128 spaces. In the systems described hereinafter, shift registers having the aforementioned structure are used as digital delay lines. In order to delay an m-bit digital word by one pulse repetition period, m N-bit shift registers are required, all operating at the timing frequency $f_c$.

In the previously-described example, the input signals A, B and A', B' of discriminator 73 are in digital form. If the ultrasound pulse echo device is constructed differently, the signals can also be in analog form. In both cases the input signals A, B or A', B' can be derived, e.g. in binary or ternary code, from the existant signals in known manner as follows:

Binary signals A and B can be generated from corresponding analog signals, e.g. using voltage comparators such as LM 311 manufactured by National Semiconductors Limited; the sign bit is obtained in simple manner from a "two's complement" coded digital signal. As shown in FIG. 16, the resulting binary coded signals A and B are each delayed by a pulse repetition period by a suitable shift register system 24 containing shift registers 71, 72 in FIG. 7 and having a storage capacity of $2 \times N$ bits, thus generating the delayed binary-coded signals A' and B'.

Ternary signals A and B can likewise be derived from corresponding analog signals using two voltage comparators in each case. Two digital comparators (constructed from the Texas Instruments SN 7485 circuit) can be used for generating ternary coded signals A and B from a digital signal. The ternary coded signals A and B are delayed by shift register system 24, which is given a storage capacity of $4 \times 10$ bits for the purpose, in order to generate the delayed binary-coded signals A' and B'.

It will be assumed hereinafter that the input signals A, B and A', B' are supplied in a suitable form for processing. i.e. in binary or ternary code, to the inputs of discriminator 73. Usually, the signal processing brought about in discriminator 73 can also be applied to input signals having higher resolution. For many applications this may be appropriate, but a more expensive circuit is required.

Discriminator for binary coded input signals

The input signals A, B and A', B' are each a digital one-bit signal bearing the sign information of the signal from which it has been derived. The input signals are supplied to the phase difference detector 11 which in the present example comprises a combining circuit which combines signals A, B, A', B' to obtain two output signals Re and Im which together bear the information about the phase difference between the vectors formed by A, B and A', B', in that Re and Im define a vector having a phase (relative to the Re axis) corresponding to the aforementioned phase difference. Owing to the rough quantization of A, B and A', B', only four different pairs of numbers Re, Im are possible.

FIG. 17 shows the truth table of the combination brought about by means of the aforementioned combining circuit. In this table, the binary "two's complement" coded equivalents are given in brackets.

Figure 18:
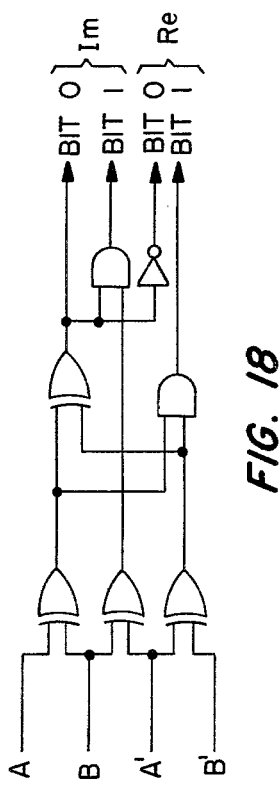
Figure 19:
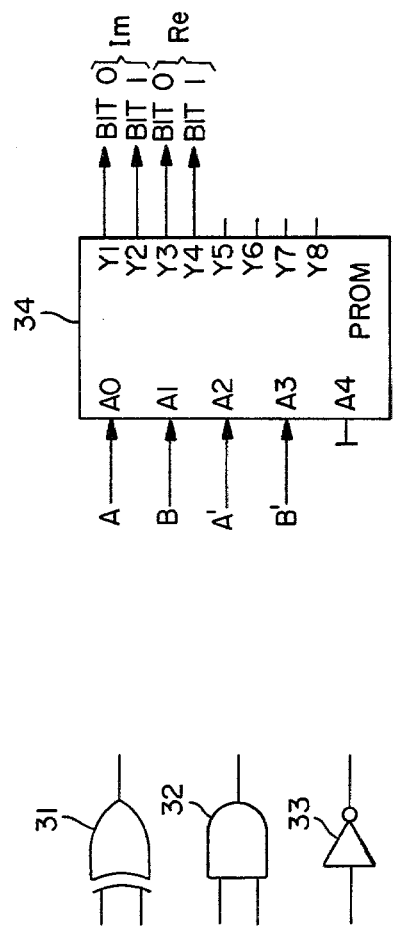
FIG. 19 shows the graphic symbols used to represent the gates in FIG. 18.

FIG. 18 shows the use of gates for combination according to the truth table in FIG. 17. FIG. 19 shows the symbols used in FIG. 18, i.e. an exclusive-OR gate 31 (the Texas Instruments integrated circuit SN 7486 contains four such gates), an AND gate 32 (the Texas Instruments SN 7408 integrated circuit contains four such gates) and an inverter 33 (the Texas Instruments SN 7404 integrated circuit contains six such inverters).

Figure 21:
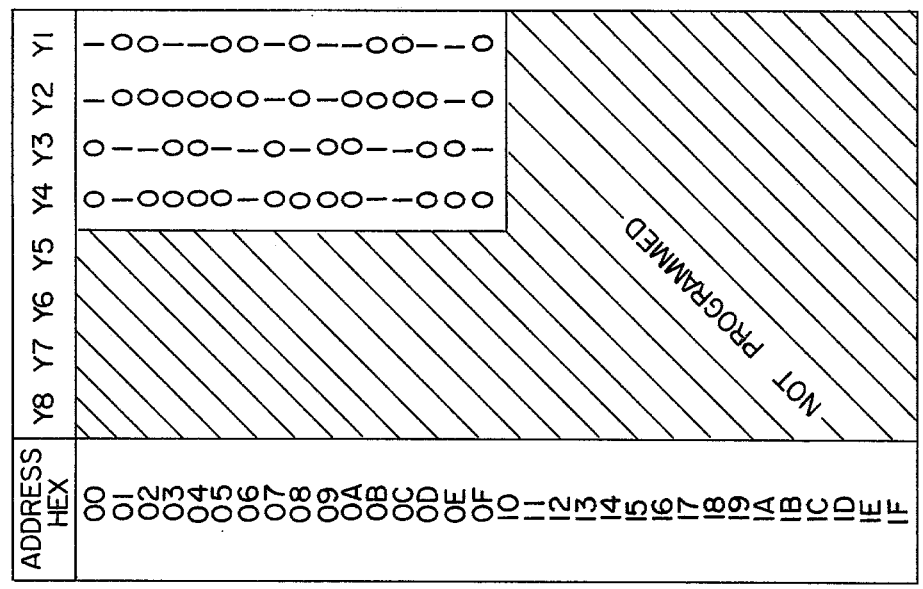
FIG. 21 shows the programming of the PROM of FIG. 20.
Figure 20:
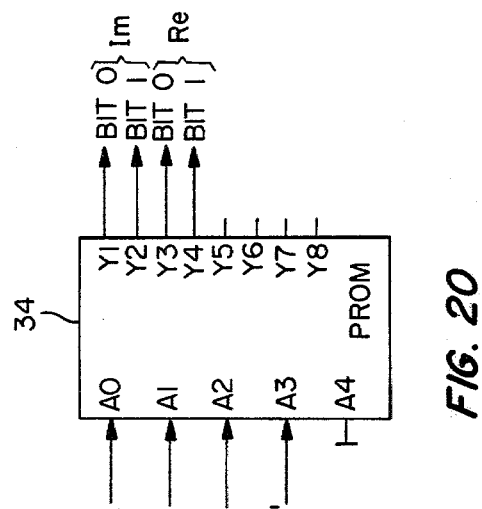
FIGS. 18, 20 and 24 illustrate alternate embodiments of phase detector 11.

As shown in FIG. 20, combination in accordance with the truth table in FIG. 17 can also be brought about by using a PROM 34, e.g. Texas Instruments integrated circuit SN 74 S288. The required programming of the PROM is shown in FIG. 21.

Figure 22:
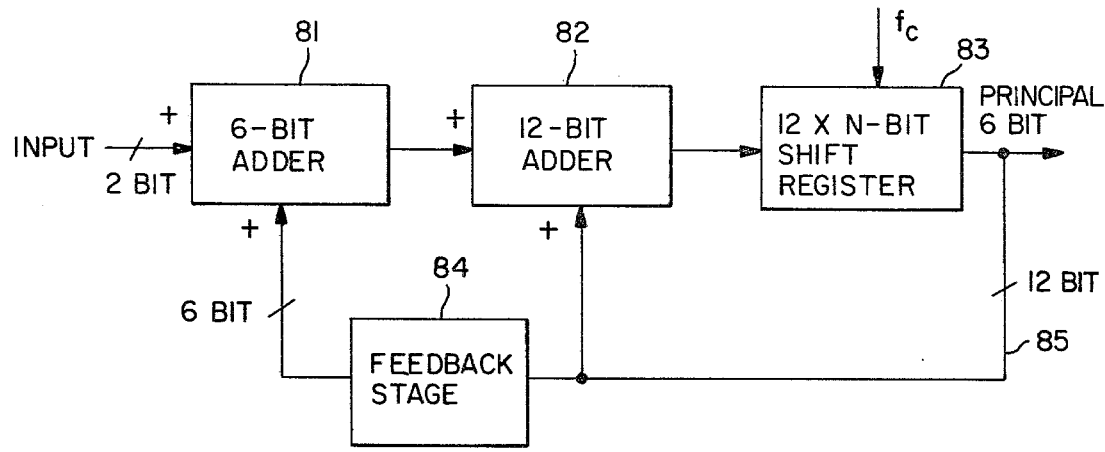
FIG. 22 shows a block diagram of the circuit labeled "SWEEP INTEGRATOR" in FIG. 12.

The signals Re and Im generated by phase difference detector 11 are averaged, either continuously by a periodic low-phase filter or by integrating a certain number of successive pulses and subsequently erasing all the stores used for integration. FIG. 22, by way of example, shows the averaging circuit of a damping sweep integrator corresponding to an N-channel first-order low-pass filter. The sweep integrator contains a six-bit adder 81 (constructed e.g. from two Texas Instruments SN 74283 integrated circuits), a 12-bit adder 82 (constructed e.g. from three Texas Instruments SN 74283 integrated circuits), a $12 \times N$-bit shift register 83 controlled by the timing frequency $f_c$ and acting as a delay line (see description of FIGS. 14 and 15 hereinbefore) and a feedback stage 84.

The 2-bit input signal (Re or Im) is supplied to the adder 81. The 12-bit output signal 85 of shift register 83 is multiplied by a constant K in the feedback stage and the product is returned to adder 81. The time constant of the sweep integrator 12 (see FIG. 12) shown in its entirety in FIG. 22 is $1/(1-K)$ pulse repetition periods.

Since a time constant of 64 pulse repetition periods is required in the present example, we put K=63/64. Multiplication of the 12-bit output signal 85 by the last-mentioned value of K is simplified if the product (63/64)·x is replaced by the difference x−1/64 x, where (63/64)·x=x−1/64 x. Multiplication by the factor −1/64 is brought about by stage 84 and adder 81 by shifting bits through six positions, followed by the formation of the "two's complement" by bit-wise inversion and adding one to the lowest "carry" input of adder 81. If the output signal has a resolution of 6 bits, the delay line must operate with 12 bits so that decay to 0 is possible.

After being averaged in the sweep integrator 12, 13, the signals Re and Im are evaluated in computer unit 14. Unit 14 can most easily be constructed from fixed-value stores (ROM's).

The calculation of velocity in unit 14 is as follows: $V = \overline{\Delta\phi}$ is the nearest integer to $\overline{Im}/[\overline{/Re/} + \overline{/Im/}]$ for $\overline{Re} \geq 0$ $2 \cdot \text{signum } [\overline{Im}] - \overline{Im}/[\overline{/Re/} + \overline{/Im/}]$ for $Re < 0$.

$|\Delta\phi|$ is calculated as follows:

$$\Delta\phi = \sqrt{|\overline{Re}|^2 + |\overline{Im}|^2}$$

The velocity must be calculated at a resolution of 8 bits, whereas a resolution of 4 bits is sufficient for its modulus.

We shall now, by way of example, describe the case where the velocity modulus must not exceed a given limiting value if the calculation is to be valid. Otherwise, the starting value is put at zero. The complete evaluation of $\overline{Re}$ and $\overline{Im}$ is therefore as follows:

Input signal $\overline{Re}$: 6-bit two's complement code corresponding to the numerical range from −32 to +31.

Input signal $\overline{Im}$: Same format as $\overline{Re}$.

Output signal V: 8-bit two's complement code corresponding to the numerical range from −127 to +127.

The output signal V must be calibrated. If the ultrasonic frequency is 4 MHz and $f_R = 10$ kHz, the range ±127 is equivalent to ±1 m/s.

In order to produce a flow profile on an observation monitor, signal V must be converted to output signal 59 (FIG. 7) using a digital-to-analog converter.

Figure 23:
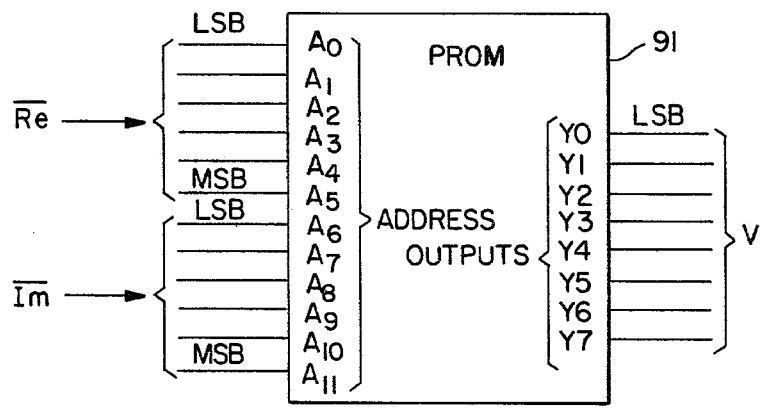
FIG. 23 shows the construction of computer unit 14 in FIG. 12, using a ROM.

FIG. 23 shows how a PROM (programmable read-only memory) 91 is used as a computer unit 14 (see FIG. 12). The PROM 91, which can contain 4096 8-bit words, is made up e.g. of 4 Intel 4×2708 integrated circuits. The lines with the LSB ("least significant bit") and MSB ("most significant bit") are marked by the corresponding abbreviations in FIG. 23.

The PROM 91's are programmed in accordance with the following formula:
If $$\sqrt{\overline{Im}^2 + \overline{Re}^2} < 15$$

then V=0 otherwise V is the nearest integer to $$127 \cdot \frac{\overline{Im}}{|\overline{Im}| + |\overline{Re}|}$$

for R>0 or $$127 \cdot \left[2 \cdot \text{signum } \frac{(\overline{Im})}{|\overline{Re}| + |\overline{Im}|} - \frac{\overline{Im}}{|\overline{Re}| + |\overline{Im}|}\right]$$

for Re<0.

V is coded by an 8-bit two's complement code.

Discriminator for ternary-coded input signals

A, B and A', B' are each a digital two-bit signal which can assume three states, depending whether the input signal is in a small region around 0 or is above the upper limit of this region or is below the lower limit. These three cases are expressed in code by the numbers 0 (binary 11); +1 (binary 01) and −1 (binary 11) respectively.

Figure 24:
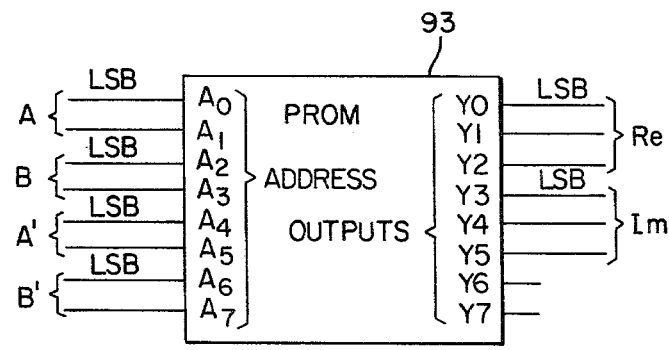
Figure 25:
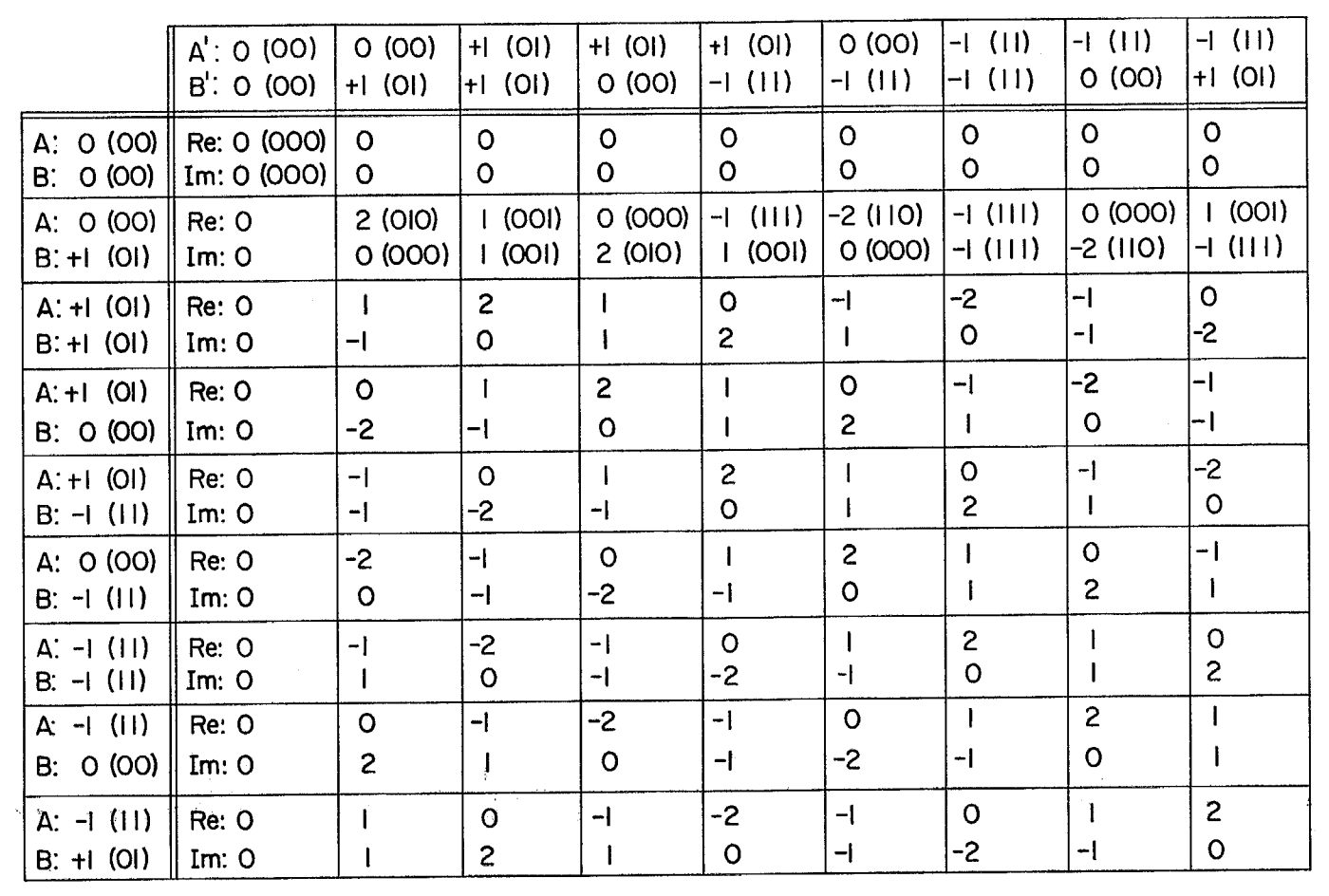

In that case the shift register 24 in FIG. 16 has a capacity of 4×N bits and the output signals Re and Im of the phase difference detector 11 each have 3 bits. The circuit for combining A, B and A', B' may most advantageously be constructed from a PROM 93. 8 address inputs and 6 data outputs are required. Use may be made, for example, of the Texas Instruments SN 74S470 PROM. FIG. 24 shows the corresponding circuitry. FIG. 25 shows the function table from which the programming of the PROMs can easily be derived. In this table, the binary "two's complement" coded equivalent is given in brackets in each case.

Re and Im are averaged by the circuit in FIG. 22, except that the input signal has a resolution of 3 bits.

The computer unit 14 is identical with the unit 14 in the discriminator for binary coded input signals (see FIG. 23).

The advantage of the last-mentioned method, using ternary-coded input signals A, B and A', B', is that if there is no Doppler signal, the modulus $$\sqrt{\overline{Im}^2 + \overline{Re}^2}$$

reliably approaches zero, since the remaining small noise signals often occur in the narrow region around the origin. In that case A and B are each zero and Re and Im are also zero after combination,. If, on the other hand, the Doppler signals are strong, this method has practically no advantages over the method using binary-coded input signals.

Improvement of the linearity

Figure 26:
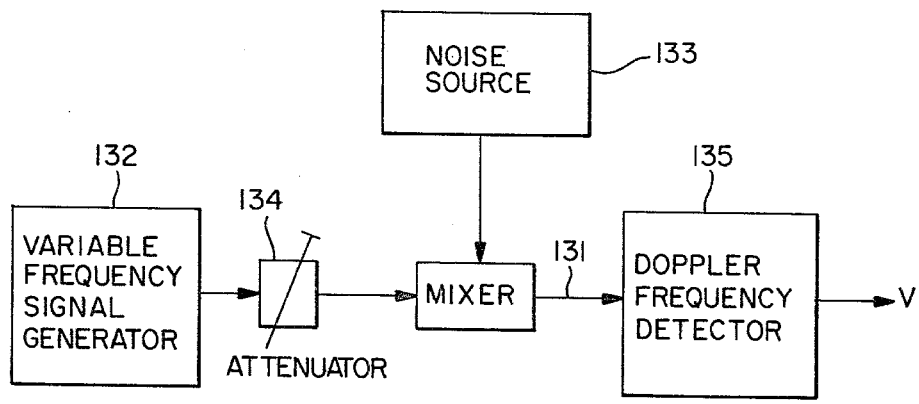
FIG. 26 shows a device for measuring the amplitude-frequency characteristics of a Doppler-frequency detector.
Figure 27:
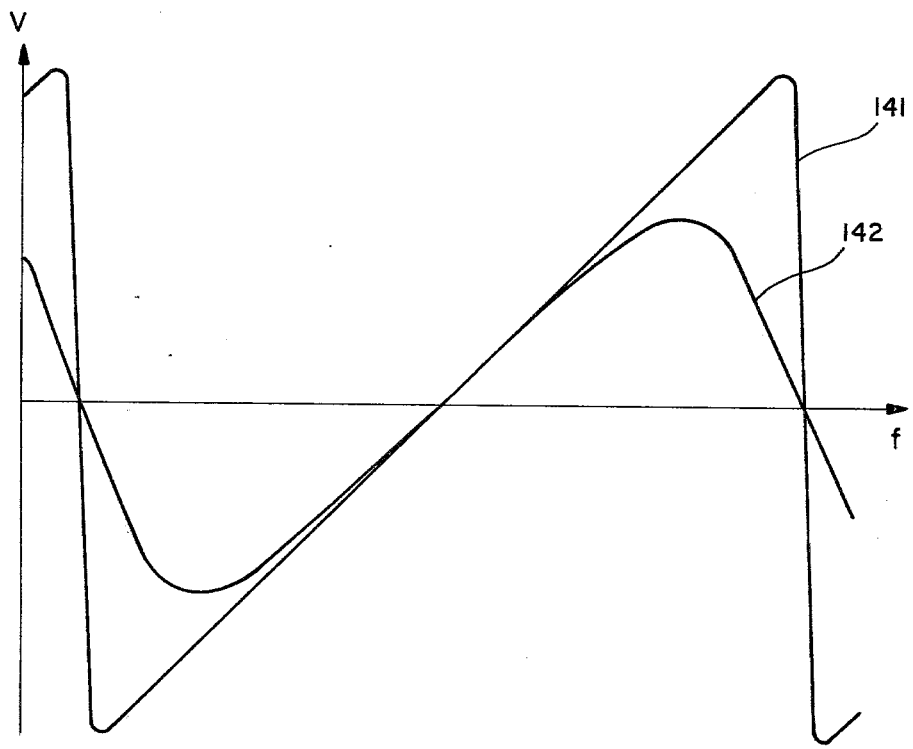
FIG. 27 shows the measured velocity-frequency characteristic of a "zero crossing counter"
Figure 28:
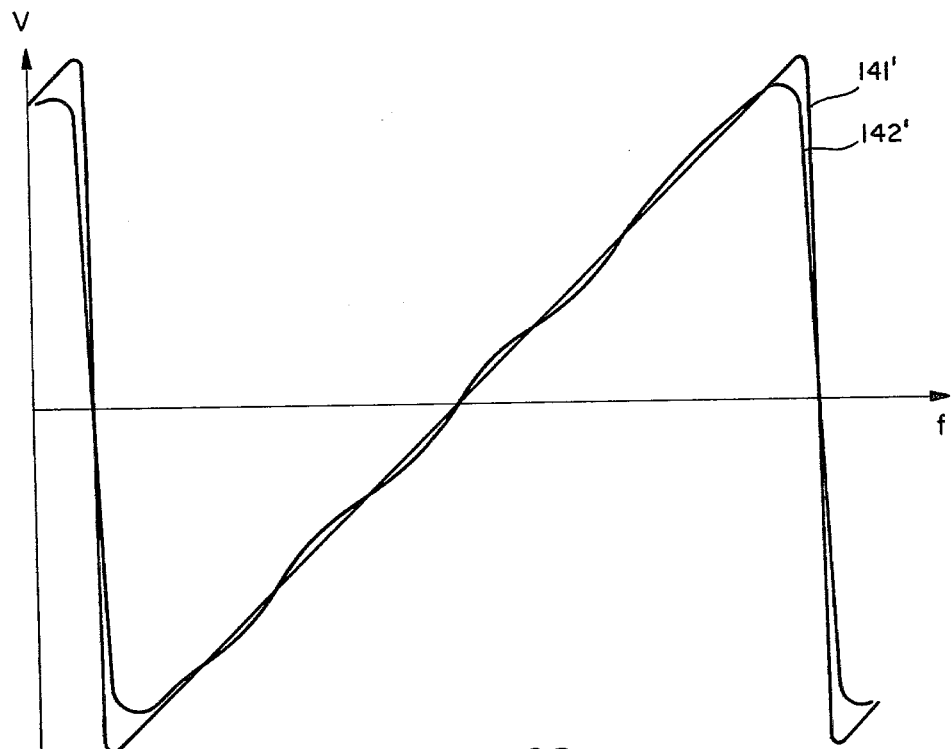
FIG. 28 shows the measured velocity-frequency characteristic of the device in FIG. 7.

The improvement in the linearity of measurement obtaining by the aforementioned discriminator 73 for binary-coded input signals can be seen by comparing the measured results in FIGS. 27 and 28. These results were obtained with the measuring circuit in FIG. 26 under similar conditions. As diagrammatically shown in the drawings, an input signal 131 corresponding to signal 55 in FIG. 7 is obtained by superposing a noise source 133 on the output signal from a variable-frequency signal generator 132. The signal-noise ratio can be adjusted by a variable attenuator 134. The input signal 131 is supplied to a Doppler frequency detector 135.

FIG. 27 shows the velocity-frequency characteristic 141 of output signal 59 with a signal/noise ratio of 26 dB, and the same characteristic 142 measured with a signal/noise ratio of 6 dB, the Doppler frequency detector being a "zero crossing counter" constructed in accordance with McLeod, "A Multiple Gate Pulse Doppler Flowmeter", 1971 IEEE Ultrasonics Symposium, Miami Beach, Fla.

FIG. 28 shows the characteristics 141', 142' measured at the same signal/noise ratios (26 dB and 6 dB respectively) when the device in FIG. 7, comprising the aforementioned discriminator 73, is used as the Doppler frequency detector. It can be seen that the last-mentioned system is relatively independent of the signal/noise ratio.

Variant of discriminator 73

Figure 29:
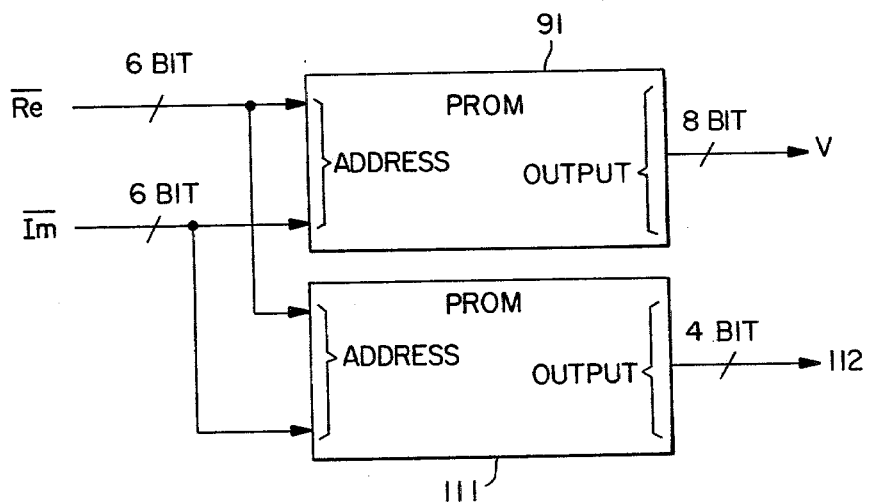
FIG. 29 shows an embodiment of the computer unit 14 for indicating turbulence.

FIG. 29 shows an embodiment of the computer unit 14 (see FIG. 12) of discriminator 73. This embodiment can produce a display which indicates the turbulence of the measured flow.

As already mentioned, the inputs of computer unit 14 are supplied with signals $\overline{Re}$ and $\overline{Im}$ corresponding to the mean value of the individual phase difference vectors defined by Re and Im.

If the signal quality is good and the flow is steady, the results Re, Im of combining the input signals A, B, A', B' are constant, so that the modulus of the averaged phase difference vector is equal to the sum of the moduli of the individual phase difference vectors. We then have:

$$\sum_{i=0}^{n}(Re_i, Im_i) = nRe, nIm$$

and $\sqrt{\overline{Re^2} + \overline{Im^2}} = n\sqrt{Re^2 + Im^2}$

If, however, the individual phase difference vectors Re, Im have a statistical fluctuation, then $$\sqrt{\overline{Re^2} + \overline{Im^2}} < n\sqrt{Re^2 + Im^2}$$

The statical fluctuation can have two causes:
(1) A bad signal/noise voltage ratio of the signal or
(2) A turbulent flow.

If cause (1) can be ruled out (e.g. by a high transmitted power and/or a highly sensitive receiver), the only possible cause of statistical fluctuation is turbulent flow.

In the case with binary coded input signals A, B, A', B', $$\sqrt{Re^2 + Im^2} = 1$$

is true for all Re, Im combinations. (In the case of ternary coding, this is only approximately true).

We thus have:

$$\sqrt{\frac{\overline{Re^2} + \overline{Im^2}}{n}}.$$

As shown in FIG. 29, the aforementioned embodiment of computer unit 14 contains the PROM 91, previously shown in FIG. 23, which generates the output signal V, and a PROM 111 which generates an output signal 112 proportional to $$\sqrt{\frac{\overline{Re^2} + \overline{Im^2}}{n}}$$

the proportionality factor being e.g. 15.

The number of averaged measured values (Re,Im) must be known and equal to n.

If the signals $\overline{Re}$ and $\overline{Im}$ are generated by the low-pass filter shown in FIG. 22, it is possible to calculate a number N=1/1−K which expresses the number of averaged measurements of Re or Im, K being the multiplier in the feedback of the low-pass filter (the averaging circuit). In the example in FIG. 22, K=63/64 and therefore n=64.

Figure 30:
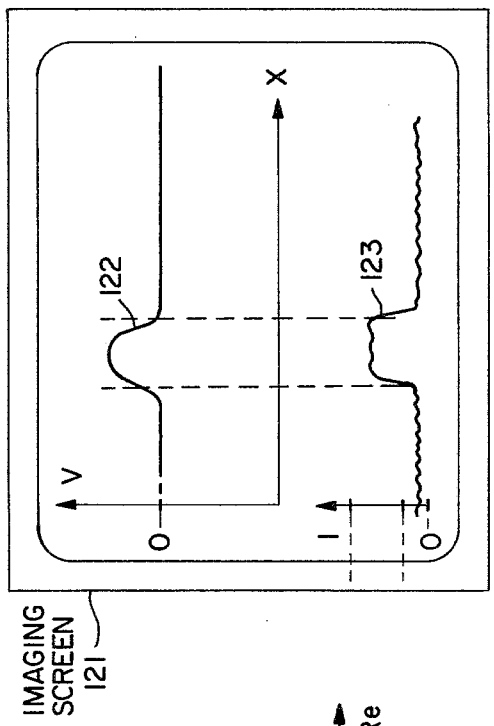
FIG. 30 is a diagram of the display produced by the device according to the invention.

FIG. 30 is a diagram of the aforementioned display, which can be obtained by using an imaging screen 121 and the embodiment of the computer unit 14 shown in FIG. 29. The display shows a velocity profile 122 of the measured flow and the turbulence 123 of the flow, i.e., a display of the signal 112 which represents the value of $$\left(\sqrt{\overline{Re^2} + \overline{Im^2}}\right)/n.$$

Profile 122 corresponds to the curve of the output signal 59 of discriminator 73 and is plotted on calibrated axes V-X, where V is the instantaneous velocity and X is the distance between the ultrasound transducer and the point at which the instantaneous velocity is measured. Display 123 corresponds to the curve of signal 112 (FIG. 29) and can have two different meanings, depending whether it relates to points outside or inside the measured flow. In the case of points outside the measured flow, i.e. those regions of profile 122 at which V=0, visible values of 123 may mean that the input signals A, B, A', B' have a good signal/noise ratio (if 123 tends towards 1) or a relatively bad signal/noise ratio (if 123 tends towards zero). If a moving-target indicator of the previously-described kind is used, display 123 will always tend towards zero for points outside the flow, since signals A, B and A', B' consist almost entirely of noise. In the case of points inside the measured flow, display 123 indicates the turbulence of the flow in the cross-section under observation. As shown in FIG. 30 a vertical axis is drawn near display 123 and shows the point 0 and 1 which are important in interpreting display 123. If 123 is near unity, the flow can be regarded as laminar. In other cases it is regarded as turbulent.

General embodiment of the phase difference detector 11

As already mentioned, the phase difference detector 11 of discriminator 73 (FIG. 12) is used to form a complex number $$Z_1 = A + jB$$

$$Z_2 = A' + jB'$$

for the input signals A, B and A', B' respectively, and a complex number $$Re + jIm = \frac{A + jB}{A' + jB'}$$

by forming the quotients $Z_1/Z_2$ of the previously-given two numbers, the components Re and Im being identical with the components of the phase difference vector $\overline{\Delta\phi}$. Detector 11 also generates output signals corresponding to the components Re and Im.

Figure 31:
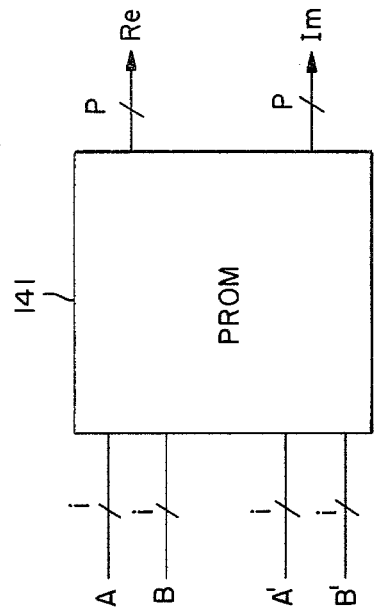
FIG. 31 shows the phase difference detector 11 in FIG. 12, comprising a PROM or a PROM system.

As shown in FIG. 31, in the case where A, B, A' and B' are i-bit binary numbers, as a phase difference detector of the aforementioned kind can be constructed from a PROM 141 in which the values of Re and Im are stored for all possible combinations of A, B, A' and B'. If each input signal has i bits and each output signal (Re and Im) has p bits, there are $2^{4i}$ solutions for Im and Re and the required PROM format is $2^{4i} \times 2p$.

The construction of the phase difference detector, using a PROM for binary or ternary coded input signals A, B, A', B', has already been described with reference to FIGS. 20, 21, 24 and 25.

In the case of binary coded input signals, i=1, p=2 and the required PROM format is $16 \times 4$ bits.

In the case of ternary-coded input signals, i=2, p=3 and the required PROM format is $256 \times 6$ bits.

If i=4 and p=5, the required PROM format is $2^{16} \times 10$ bits = $64k \times 10$ bits. Since the largest PROM available at present has a capacity of $8k \times 8$ bits, 10 of them are required. To reduce this expense, it is advantageous to express the complex number Re +j Im as follows:

$$Re + jIm = \frac{A + jB}{A' + jB'} \cdot \frac{A' - jB'}{A' - jB'} =$$

$$\frac{A \cdot A' + B \cdot B' + j(BA' - AB')}{A'^2 + B'^2}$$

$$Re = \frac{A \cdot A' + B \cdot B'}{A'^2 + B'^2} = \frac{\|A\|}{A' \times B'^2/A} + \frac{B}{A'^2/B' + B'}$$

$$Im = \frac{B \cdot A' - A \cdot B'}{A'^2 + B'^2} = \frac{B}{A' + B'^2/A'} - \frac{A}{A'^2/B' + B'}$$

Figure 32:
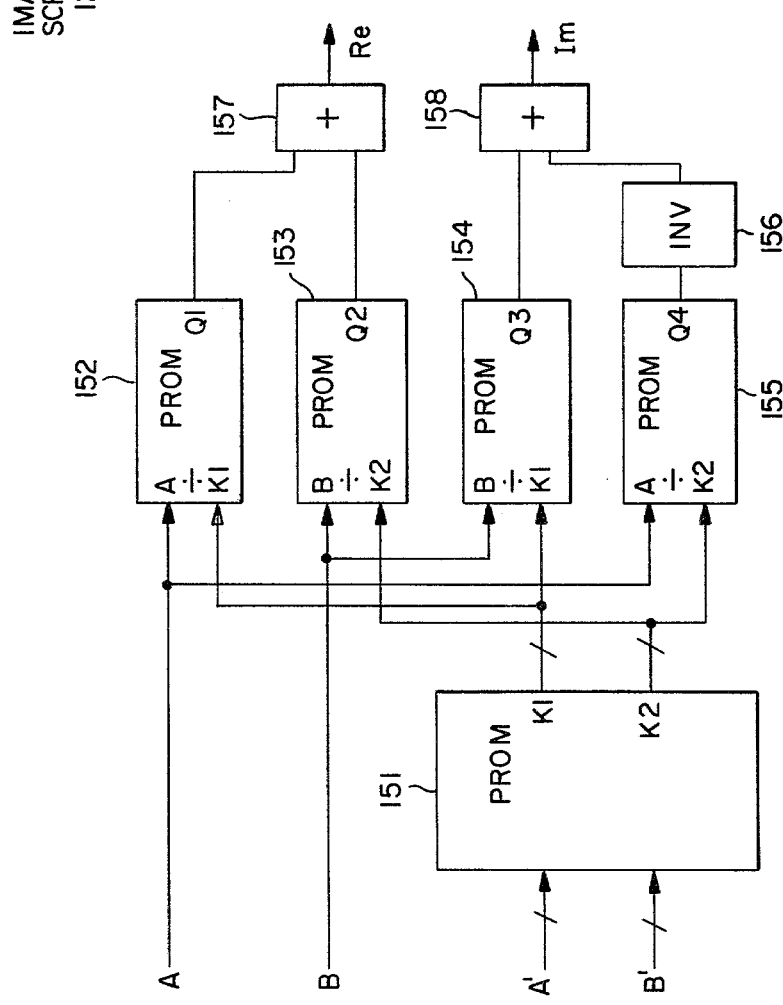
FIG. 32 shows a simplified circuit for constructing the phase difference detector 11, using PROM units.

By means of this conversion, the output signals Re and Im can now be generated by the phase difference detector circuit shown in FIG. 32. The circuit comprises 5 PROM's 151–155, an inverter 156 and two adders 157,158.

The PROM 151 generates output signals corresponding to the values:

$$K1 = A' + B'^2/A'$$

$$K2 = A'^2/B' + B'$$

If signals A', B' and $K_1$, $K_2$ have a resolution of i bits, PROM 151 must have the format $2^{2i} \times 2i$.

The four PROM's 152–155, each having a format of $2^{2i} \times i$, form output signals corresponding to the quotients $Q_1 = A/K1$
$Q_2 = B/K2$
$Q_3 = B/K1$
$Q_4 = A/K2$ Next, inverter 156 and adders 157, 158 form the output signals $Re = Q_1 + Q_2$
$Im = Q_3 - Q_4$ In the example with i=4 and p=5, using the circuit according to FIG. 32, 1 256×8 bit PROM
4 256×4 bit PROMs
1 inverter-IC, e.g. Texas Instruments SN 7404, and
2 adders, e.g. Texas Instrument SN 74283 are required, i.e. the storage requirement is reduced from 640 kbits to 6 kbits, compared with the direct calculation of Re and Im in the system in FIG. 31.

I claim:

1. A method of determining flow velocities of flow material by measuring the phase difference between Doppler signals derived from wave pulses which are reflected by substantially one and the same reflector, which is an element of the flow material, at two different times, the interval between the times being predetermined, the Doppler signals carrying flow velocity information, each Doppler signal being demodulated in quadrature to produce a pair of electrical signals which jointly bear information representative of the phase of the Doppler signal, characterized in that it comprises:
   (a) combining at least a first and a second pair of said electrical signals to produce a third pair of electrical signals which together bear information representative of the magnitude and sign of the phase difference between the Doppler signals from which the first and second pair of electrical signals are derived;
   (b) forming mean-value signals, each corresponding to the mean value of one of the signals from said third pair of electrical signals; and
   (c) combining the mean-value signals to form an output signal which corresponds to the magnitude and sign of the average value of the phase difference between the Doppler signals, and thereby is representative of the flow velocity at the location of the reflector.

2. A method according to claim 1, wherein the first and second pair of electric signals can have only two discrete values, so that each pair of signals defines a quadrant of the total angular range, i.e. from 0° to 360°.

3. A method according to claim 1 wherein the third pair of signals can have the values of 0, +1 and −1, so that the phase angle of the vector defined by the third pair of signals can have the values 0°, 45°, 90°, 135°, 180°, 225°, 270° and 315°.

4. A device for determining flow velocities of flow material by measuring the phase difference between Doppler signals derived from wave pulses which are reflected by substantially one and the same reflector, which is an element of the flow material, at two different times, the interval between the times being predetermined, the Doppler signals carrying flow velocity information, said device including quadrature demodulation means which demodulate each Doppler signal to produce a pair of electrical signals which jointly bear information representative of the phase of the Doppler signal, said device further comprising;
   (a) a logic electrical circuit, connected to the outputs of the quadrature demodulation means, for combining at least a first and a second pair of said electrical signals to produce a third pair of electrical signals which together bear information representative of the magnitude and sign of the phase difference between the Doppler signals from which the first and second pair of electrical signals are derived;
   (b) averaging circuit means, connected to the outputs of the logic electrical circuit, for forming mean-value signals, each corresponding to the mean-value of one of the signals of said third pair of electrical signals; and (c) a computer unit, connected to the outputs of said averaging means, for processing the mean-value signals to produce and output signal representative of the magnitude and sign of the average value of the phase difference between the Doppler signals, and thereby representative of the flow velocity at the location of the reflector.

5. A device according to claim 4 wherein the computer unit contains means for calculating the modulus of the sum of the vectors defined by the third pair of signals (Re, Im) for a number of Doppler signals, and means for suppressing the output signal from the computer unit, depending on the value of the calculated modulus.

6. Use of the method according to claim 4, in an ultrasound diagnostic device for determining a velocity profile of a flow.

7. Use according to claim 6 wherein the flow is the blood stream in a blood vessel.

8. A device according to claim 4 wherein the logic circuit contains means for producing the third pair of electrical signals by forming the quotient of two complex numbers defined by the first and second pair of electrical signals.

9. A device according to claim 4 wherein the computer unit contains means for generating an output signal representative of the flow turbulence as defined by the modulus of the averaged phase difference vector divided by the number of averaged third pairs of signals.

* * * * *